United States Patent [19]
Kearns et al.

[11] Patent Number: 6,156,056
[45] Date of Patent: Dec. 5, 2000

[54] SUTURE BUTTRESS

[75] Inventors: Bryan K. Kearns, Bridgewater; Steven M. Bowman, Brighton; Richard F. Wenstrom, Jr., Norwood; Mark Steckel, Braintree, all of Mass.; Edward V. Craig, New Canaan, Conn.

[73] Assignee: Ethicon, Inc., Somerville, N.J.

[21] Appl. No.: 09/206,522

[22] Filed: Dec. 7, 1998

Related U.S. Application Data

[63] Continuation-in-part of application No. 09/113,247, Jul. 10, 1998, which is a continuation-in-part of application No. 09/004,989, Jan. 9, 1998.

[51] Int. Cl.[7] ............................................. A61B 17/04
[52] U.S. Cl. ..................................... 606/232; 606/72
[58] Field of Search ............................ 606/72, 73, 148, 606/230, 231, 232

[56] References Cited

U.S. PATENT DOCUMENTS

| | | | |
|---|---|---|---|
| 3,845,772 | 11/1974 | Smith | 128/335 |
| 4,009,719 | 3/1977 | Kletschka et al. | 128/335 |
| 4,045,825 | 9/1977 | Stroot | 3/1.91 |
| 4,549,545 | 10/1985 | Levy | 128/335 |
| 4,873,976 | 10/1989 | Schreiber | 128/334 R |
| 5,366,480 | 11/1994 | Corriveau et al. | 606/233 |
| 5,423,763 | 6/1995 | Helland et al. | 604/174 |
| 5,575,801 | 11/1996 | Habermeyer et al. | 606/148 |
| 5,632,748 | 5/1997 | Beck, Jr. et al. | 606/89 |
| 5,662,654 | 9/1997 | Thompson | 606/72 |
| 5,681,333 | 10/1997 | Burkhart et al. | 606/148 |
| 5,849,004 | 12/1998 | Brumlet | 606/232 |
| 5,984,927 | 11/1999 | Wenstrom | 606/73 |

FOREIGN PATENT DOCUMENTS

WO9806344  2/1998  WIPO .

OTHER PUBLICATIONS

The Rotator Cuff Repair System Surgical Technique, Surgical technique as described by Stephen J. Snyder, M.D., Southern California Orthopedic Institute, Van Nuys, California.

"Avoid suture migration following rotator cuff repair" *Cuff Link*™, Bone Tunnel Augmentation Device, Innovasive Devices, Inc., Copyright 1997.

*Innovasive Cuff Link*™, Bone Tunnel Augmentation Device, Instructions for Use, pp. 1–3.

*Primary Examiner*—Michael A. Brown
*Attorney, Agent, or Firm*—Nutter, McClennen & Fish, LLP

[57] ABSTRACT

A suture buttress comprises a hollow tube having an outer wall, a central channel, a center line extending through the channel, leading end for insertion into a bone tunnel and a trailing end. The hollow tube is bendable into a curved tube having an outer radius and an outer radial surface, the outer radial surface defining a plurality of slits formed in the outer wall. The suture buttress further includes at least one projecting member integral with and extending outward from the outer wall. The at least one projecting member is sufficiently strong to form a friction fit within a bone tunnel. A method for using the suture buttress to attach soft tissue to bone by inserting the suture buttress into a tunnel formed in bone, passing a suture through the tunnel and suture buttress and using the suture to attach soft tissue to the bone.

32 Claims, 9 Drawing Sheets

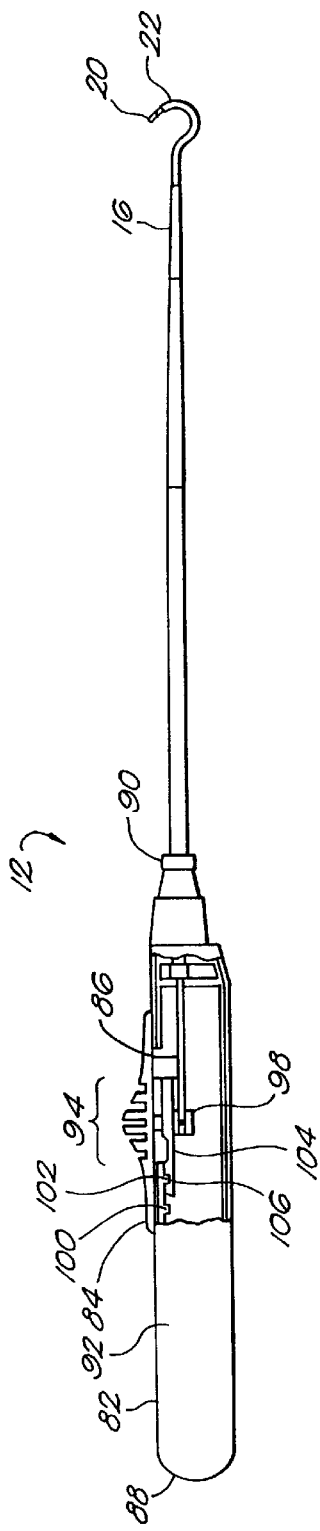
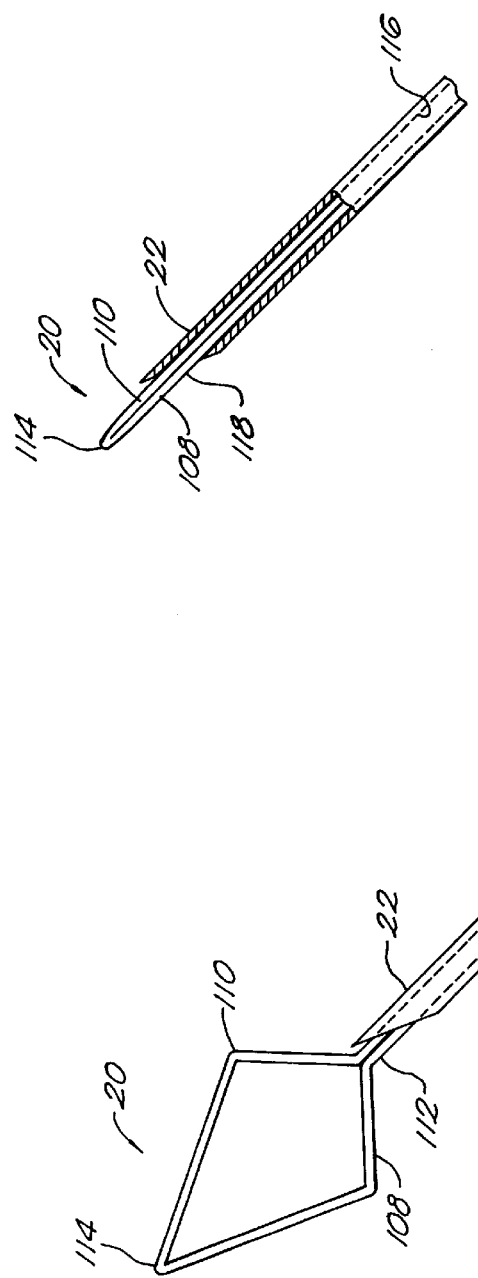
FIG. 9
FIG. 10
FIG. 11

SUTURE BUTTRESS

CROSS-REFERENCE TO RELATED APPLICATIONS

This application is a continuation-in-part of Application No. 09/113,247, filed Jul. 10, 1998, titled "SUTURE BUTTRESS", which is a continuation-in-part of Application No. 09/004,989, filed Jan. 9, 1998, titled "SUTURE BUTTRESS SYSTEM".

FIELD OF THE INVENTION

The invention relates to a suture buttress, and more particularly to a suture buttress having a securing element which retains the suture buttress within a bone tunnel.

BACKGROUND OF THE INVENTION

Open repair of the rotator cuff tendon is the most common open surgical procedure performed on the shoulder. It has been estimated that the incidence of rotator cuff tearing in the population at large runs between 15 and 25%, with approximately half of these being full thickness tears of the tendon. A smaller percentage of these become sufficiently symptomatic to warrant surgical repair.

Generally, techniques for repairing rotator cuff tears involve reattaching the torn tendon back to the bone from which it is avulsed. Typically, suture material is used to tie the tendon directly back to bone to facilitate healing of the tendon. Common technical problems with this repair often result from the fact that rotator cuff tears frequently occur in patients who are in an older age group. These patients often have poor quality bone, osteopenic bone, or bone that has been weakened by disuse due to pain. When the tendon is brought back to the bone, attempts to hold the tendon securely to the bone can be frustrated by the poor quality bone.

One method for reattaching the rotator cuff tendon to bone is to make a hole or tunnel in the bone of the greater tuberosity, to pass suture thread that has been secured to the tendon through these bone tunnels, and to reattach the rotator cuff tendon directly to the bone by tying these sutures. Using this method, the suture material can be frayed and weakened, or possibly severed, by contact with sharp edges of subcortical bone inside the bone tunnel or at the openings of the bone tunnel.

Poor bone quality also affects this method of repair adversely as the suture material may cut directly through the bone, frustrating the attempts at secure repair. Even where the suture does not cut completely through the bone, any amount of carving into bone by the suture material may result in a loosening of the suture and a corresponding loosening of the attachment of the rotator cuff tendon to bone.

SUMMARY OF THE INVENTION

The present invention provides a suture buttress including a hollow tube having an outer wall, a central channel, a center line extending through the channel, leading end for insertion into a bone tunnel and a trailing end. The hollow tube is bendable into a curved tube having an outer radius and an outer radial surface. The outer radial surface defines a plurality of slits formed in the outer wall, and the slits have a leading edge and a trailing edge corresponding to the leading end and trailing end of the tube. The suture buttress also includes at least one projecting member that is integral with and extends outward from the outer wall and is sufficiently strong to form a friction fit within a bone tunnel.

In one embodiment, the projecting member is a pyramidal projection that is adjacent to the leading edge of a slit. The suture buttress may further include a suture retriever, wherein the hollow tube is adapted to be removably and replaceably disposed on the suture retriever. The projecting member of the bone tunnel buttress is effective to allow the bone tunnel buttress to slide into a bone tunnel in a first direction when urged into the bone tunnel by the suture retriever while preventing the bone tunnel buttress from sliding out of the bone tunnel in a second direction that is substantially opposed to the first direction upon removal of the suture retriever from the bone tunnel.

At least one secondary slit may be defined on a surface of the hollow tube opposite the outer radial surface. The at least one secondary slit extends may be substantially perpendicular to the center line of the hollow tube and may extend beyond the center line. The at least one slit formed in the outer radial surface may also be substantially perpendicular to the center line of the tube and extend into the outer wall of the tube past the center line. In one embodiment, at least one secondary slit is provided between each adjacent slit in the outer radial surface. The slits allow the hollow tube to easily curve to fit within a curved bone tunnel.

Tabs may be provided on the suture buttress formed at an angle to a longitudinal axis of the suture buttress so that the tabs extend outward from the outer surface of the suture buttress. The tabs are resiliently deformable and may be recessable within cut-outs formed in the outer surface of the suture buttress, allowing the tabs to deform as the suture buttress slides into a bone tunnel in a first direction when inserted into a bone tunnel. After insertion of the suture buttress in the bone tunnel, the tabs engage the tunnel to prevent the suture buttress from sliding out of the tunnel. A flange may also be disposed on the outer surface of the buttress. The hollow tube may also be constructed of a porous material or have pores formed thereon to promote bone ingrowth in a bone tunnel.

BRIEF DESCRIPTION OF THE DRAWINGS

The invention will be more fully understood by reference to the following detailed description when considered in conjunction with the accompanying drawings, in which.

Figure 1:
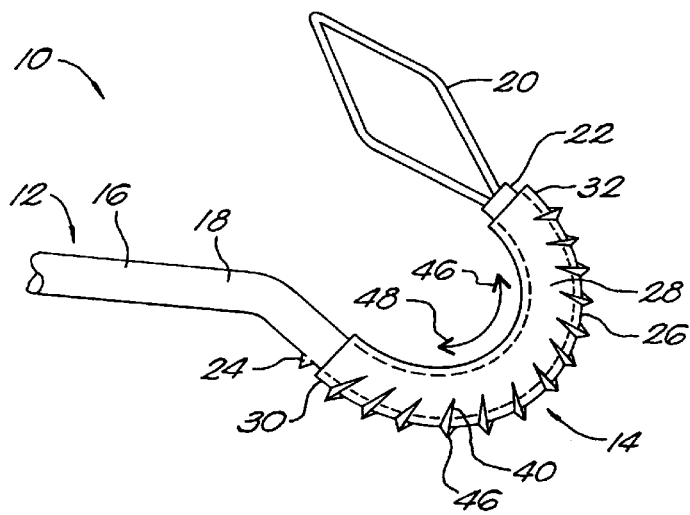
FIG. 1 is an elevated view of a suture buttress system showing a distal portion of a suture retriever, a suture buttress disposed on the retriever and a suture retaining element extending from the retriever.
Figure 3:
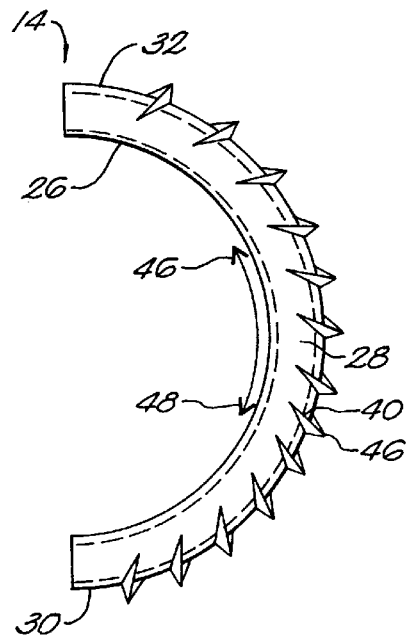
Figure 4:
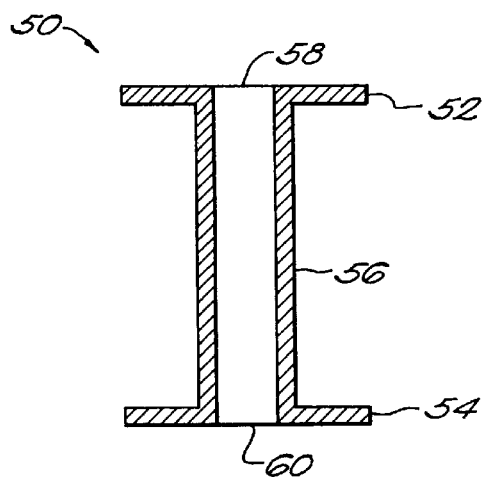
Figure 5:
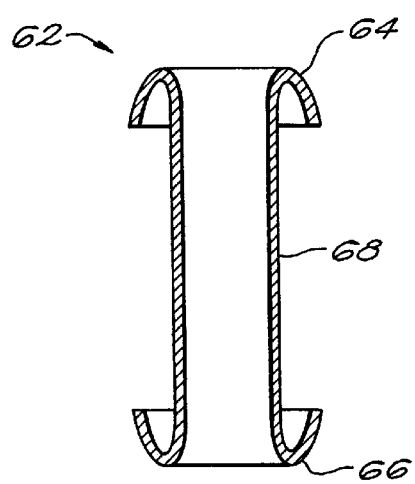
Figure 6:
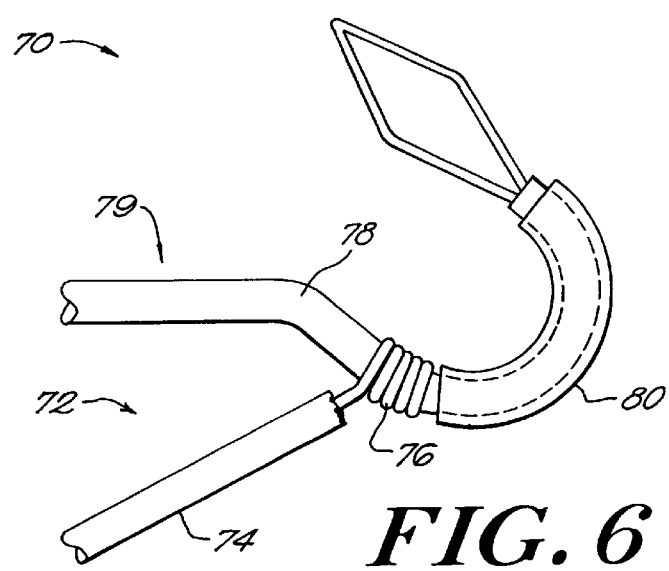
Figure 7:
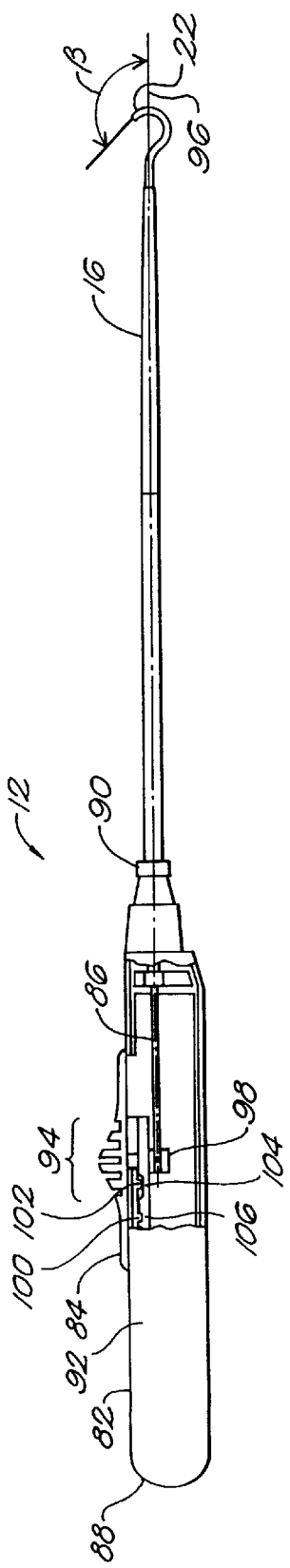
Figure 8:
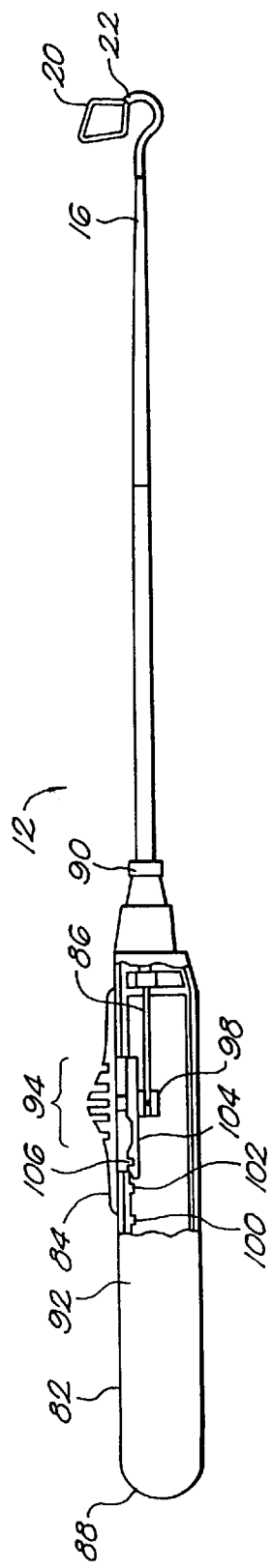
Figure 12:
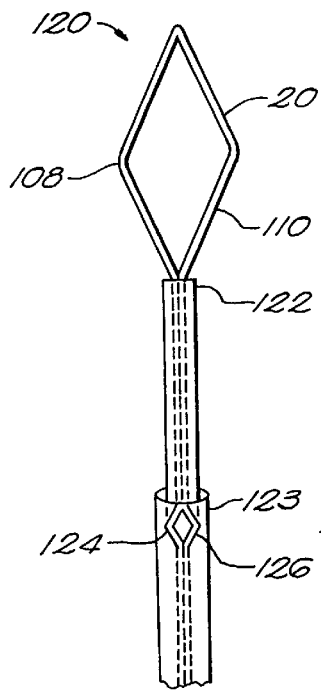
Figure 13:
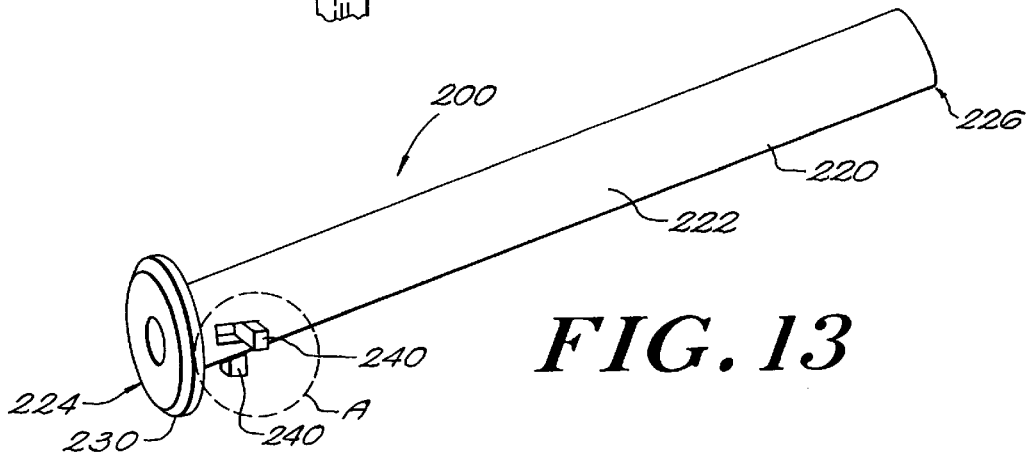
Figure 14:
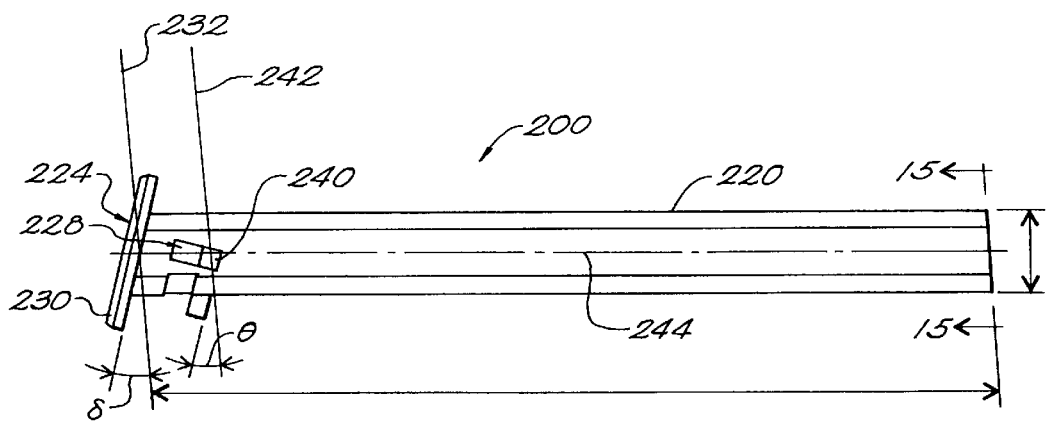
Figure 15:
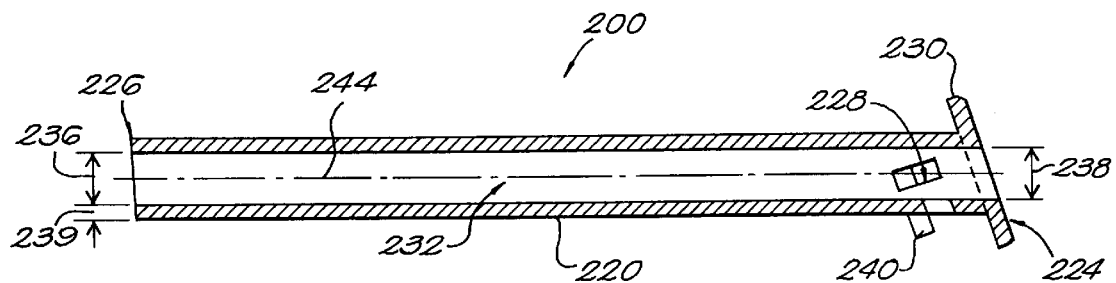
Figure 16:
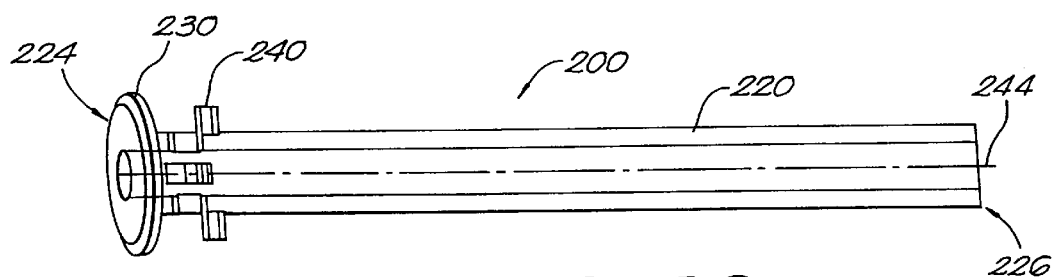
Figure 17:
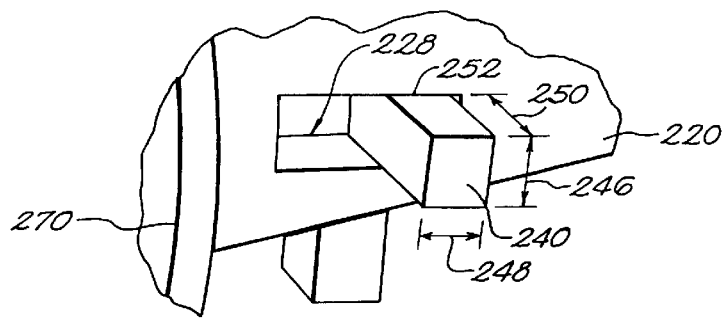
Figure 18:
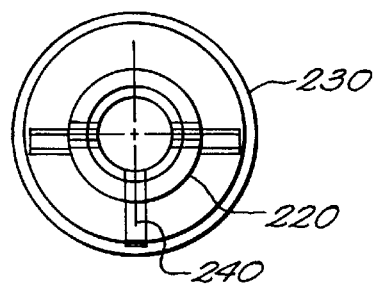
Figure 19:
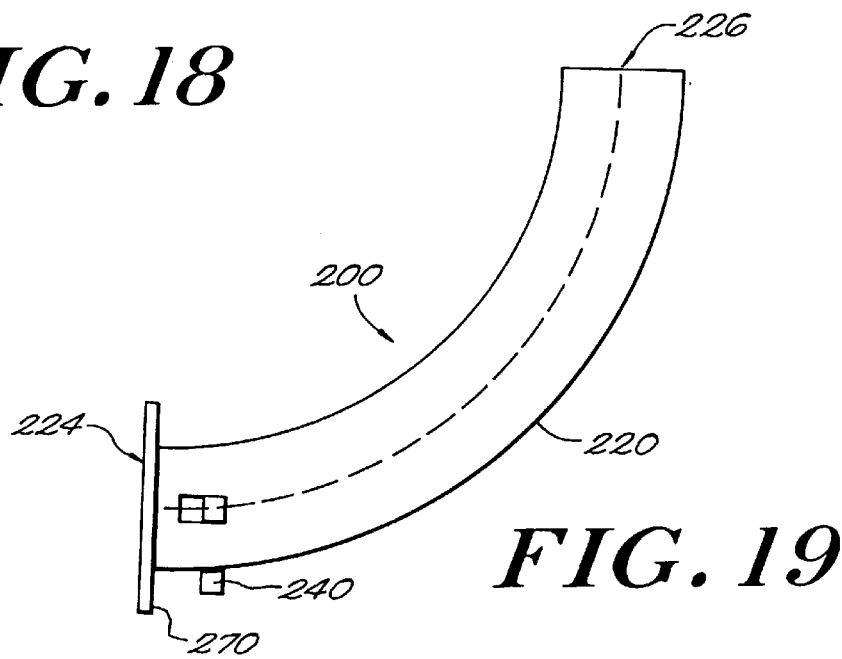
Figure 20:
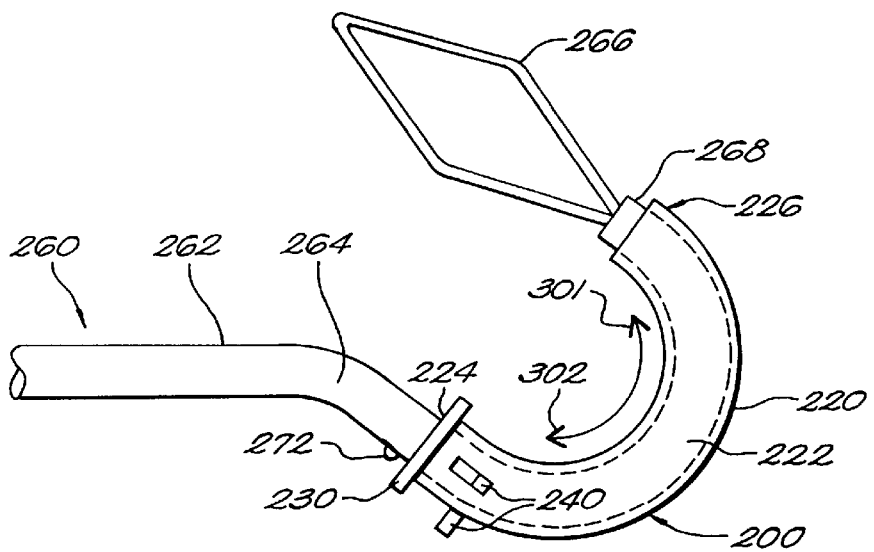
Figure 21:
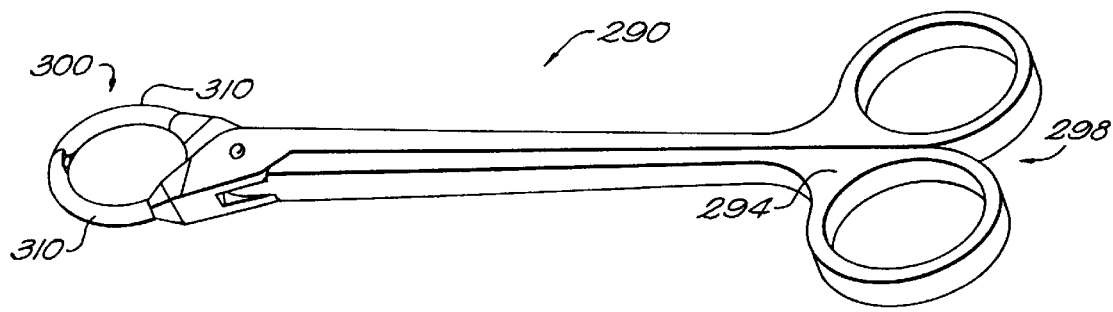
Figure 22:
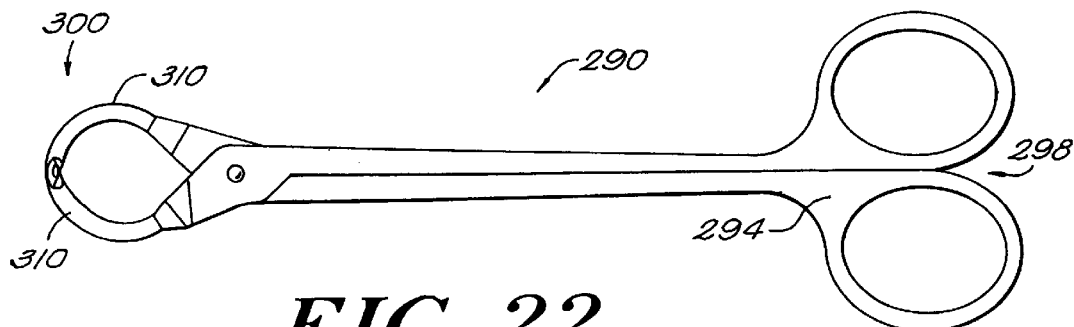
Figure 23:
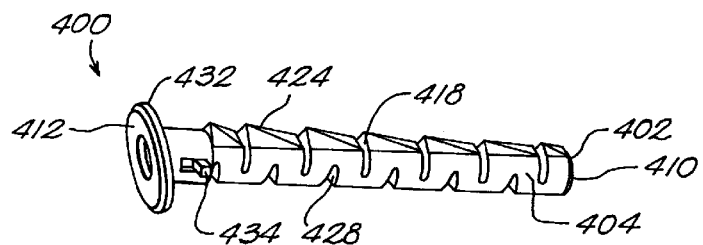
Figure 24:
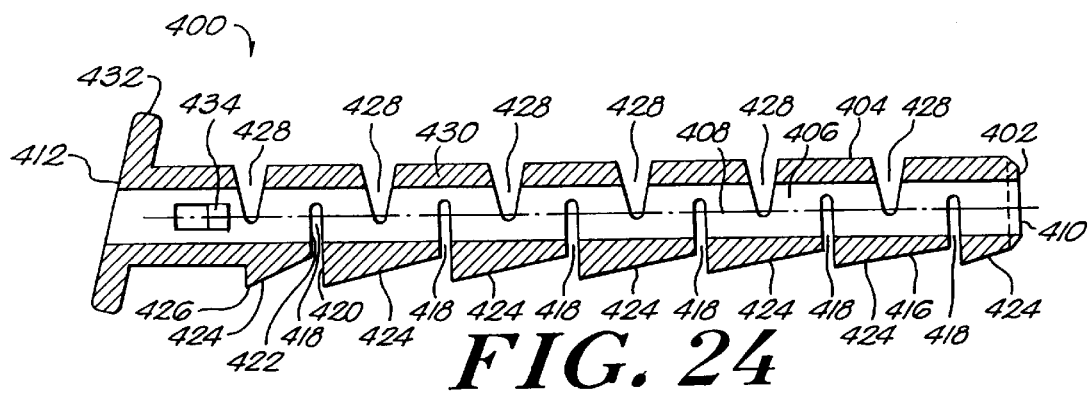
Figure 25:
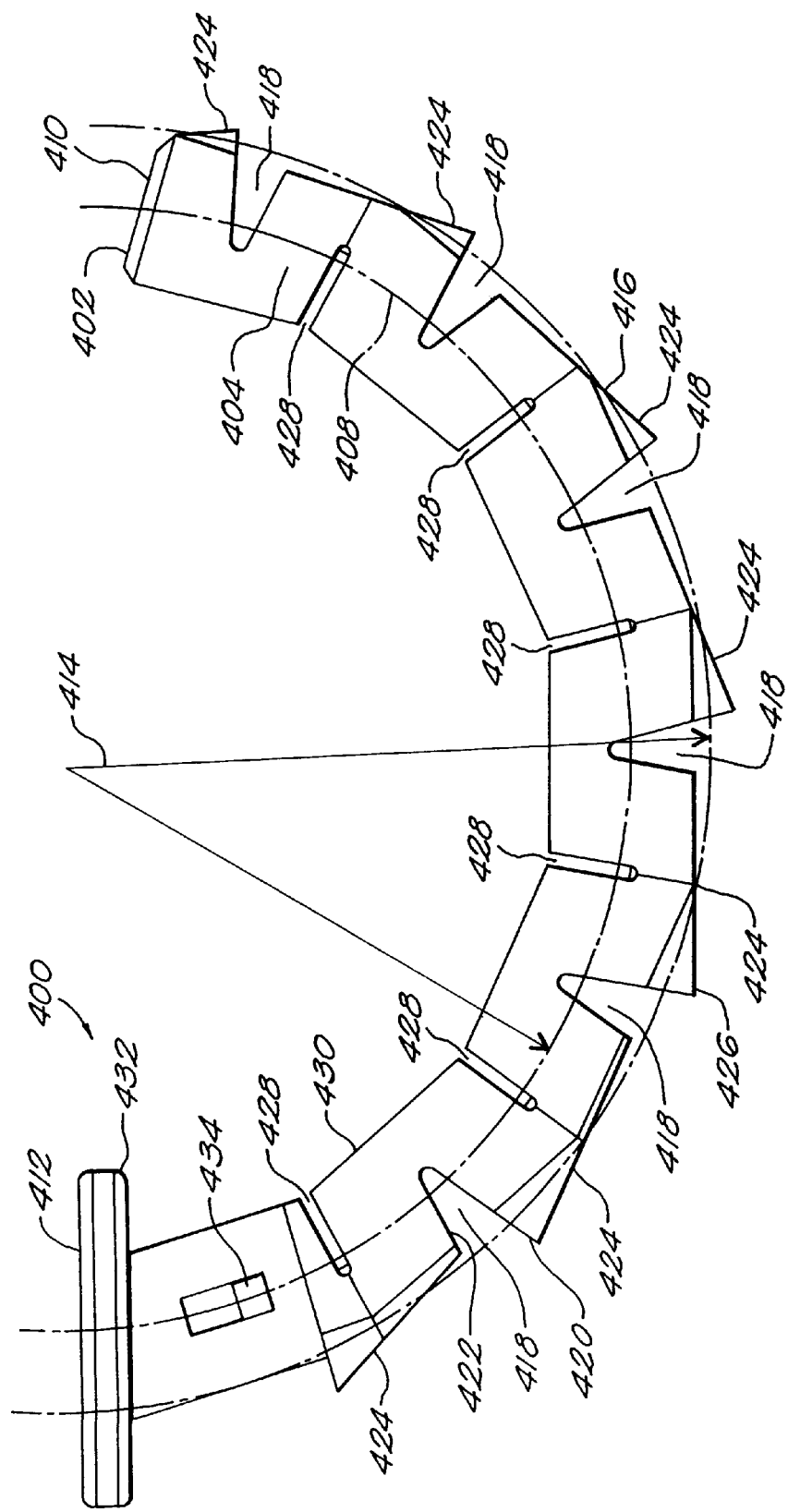

PIG. 2 is an elevated view of the suture buttress of FIG. 1 in an unflexed position;

FIG. 3 is an elevated view of the suture buttress of FIG. 1 in a flexed position;

FIG. 4 is a cross-sectional view of a suture buttress having flanges;

FIG. 5 is a cross-sectional view of a suture buttress having opposed ends folded over onto an outer surface of the buttress; and FIG. 6 is an elevated view of a suture buttress system including a suture buttress deployment tool;

FIG. 7 is an elevated view, with a partial cut-away, of the suture retriever of FIG. 1, with the suture retaining element in a retracted position;

FIG. 8 is an elevated view, with a partial cut-away, of the suture retriever of FIG. 1, with the suture retaining element in an extended position;

FIG. 9 is an elevated view, with a partial cut-away, of the suture retriever of FIG. 1, with the suture retaining element in a partially retracted, intermediate position;

FIG. 10 is an elevated view of the suture retaining element of FIG. 1 in an extended position;

FIG. 11 is an elevated view, with a partial cut-away, of the suture retaining element of FIG. 1 in an intermediate position;

FIG. 12 is an elevated view of a suture tunnel buttress system having an internal tube delivery scheme;

FIG. 13 is a perspective view of an additional suture buttress in accordance with the teachings of the present invention;

FIG. 14 is a right side view of the suture buttress of FIG. 13;

FIG. 15 is a cross sectional view of the suture buttress taken along line 15—15 in FIG. 14;

FIG. 16 is a bottom view of the suture buttress of FIG. 13;

FIG. 17 is a detailed view of portion A of the suture buttress of FIG. 13;

FIG. 18 is a rear view of the suture buttress of FIG. 13;

FIG. 19 is a side view of the suture buttress of FIG. 13 in a flexed position;

FIG. 20 is a side view of the suture buttress of FIG. 13 in conjunction with a suture retriever;

FIG. 21 is a perspective view of a suture buttress bone rasp tool;

FIG. 22 is a top view of the bone rasp tool of FIG. 21;

FIG. 23 is a perspective view of an additional suture buttress of the invention;

FIG. 24 is a cross-sectional view of the suture buttress of FIG. 23 in an unbent position; and FIG. 25 is a side view of the suture buttress of FIG. 23 in a bent or curved position.

DETAILED DESCRIPTION OF THE INVENTION

An exemplary suture buttress system 10 of the invention, illustrated in FIG. 1, includes a suture retriever 12 and a suture buttress or bone tunnel buttress 14. The suture retriever 12 has an elongate portion 16 having an outer surface 18 and a suture retrieving element 20 disposed at its distal end 22. The suture buttress 14 is removably and replaceably disposed on the outer surface 18 of the elongate member 16. A suture buttress stop 24 may also be provided on the outer surface 18 of the elongate member 16 in proximity to the suture buttress 14.

Figure 2:
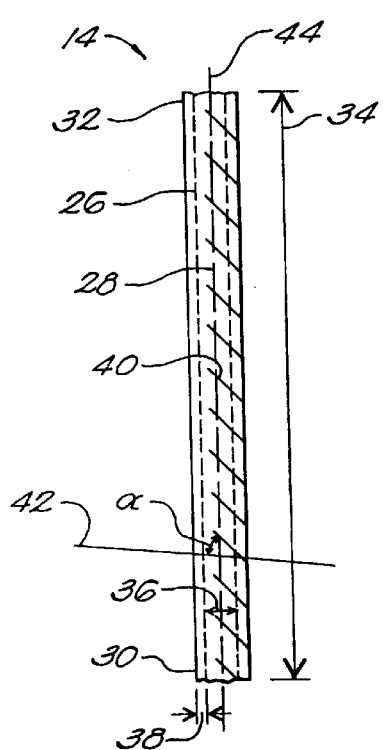

The suture buttress 14, illustrated in FIGS. 1–3, includes a resilient hollow tube 26 having an outer surface 28 and opposed proximal and distal ends 30, 32. The resilient hollow tube 26 may be made from a variety of resilient materials including absorbable and non-absorbable materials. Exemplary non-absorbable polymeric materials include polysulfone, PEEK, Nylon and Delrin. Exemplary bioabsorbable materials useful for making the resilient hollow tube 26 include homo and copolymers of glycolide and trimethylene carbonate, homo and copolymers of lactide and glycolide, homo and copolymers of polylactic acid, or a combination of these materials. Additionally, the resilient hollow tube 26 may be constructed from the same materials used to construct sutures for use in orthopedic procedures, including polydioxanone (PDS) and other materials known to those of ordinary skill in the art.

The resilient tube 26 should have sufficient length 34 to protect a suture as applied in surgical procedure and, in particular, in an orthopedic procedure where the suture is passed through a bone tunnel. Generally, where the suture buttress system 10 is used in rotator cuff repair surgery in which a suture is passed though a bone tunnel in the proximal humerus, the length 34 of the resilient tube should be between about 0.75 and 1.50 inches.

The inner diameter 36 of the resilient tube 26 should be large enough to allow the tube 26 to be removably and replaceably disposed on the outer surface 18 of the suture retriever 12 and large enough to allow a suture to be drawn through the tube 26. In addition, the inner diameter 36 must be selected so that, with an appropriate wall thickness 38, the resilient tube 26 will fit within a suitably sized bone tunnel. Generally, for use in rotator cuff repair surgery, the inner diameter 36 of the resilient tube 26 is between about 0.060 and 0.085 inch and the wall thickness 38 is between about 0.014 and 0.018 inch.

The resilient tube 26 may be provided with an external fastening element that is effective to secure it within a bone tunnel. The exemplary resilient tube 26 is provided with at least one angled slit 40 for this purpose. Each slit 40 is angled by an amount a with respect to a plane 42 that is transverse to a longitudinal axis 44 of the resilient tube 26. While the angle a may take on any value, a is preferably positive and more preferably is between about 20° and 60°. When the slits 40 are so angled, flexing the resilient tube (as shown in FIGS. 1 and 3) causes a series of raised edges 46 to extend outward from the outer surface 28 of the resilient tube 26. The edges 46 are angled so that they are easily deformed and pressed back to the outer surface 28 to allow the resilient tube 26 to slide into a bone tunnel when urged in a first direction 46 into the bone tunnel by a surgeon when inserting the suture retriever 12 into the tunnel.

The suture buttress stop 24, provided on the outer surface 18 of the elongate member 16 in proximity to the suture buttress 14, may prevent the resilient tube 26 from sliding backwards on the outer surface 18 of the elongate member 16 during insertion of the suture retriever 12 into a bone tunnel in the first direction 46. The suture buttress stop 24 may be formed by cutting out or otherwise deforming a portion of the outer surface 18 of the elongate member 16, by attachment to the outer surface 18, or in some other manner that may be selected by a person of ordinary skill in the art.

Once the resilient tube 26 has been inserted into a bone tunnel, the raised edges 46 engage the inner surface of the bone tunnel to prevent the resilient tube 26 from sliding out of the bone tunnel in a second direction 48, substantially opposed to the first direction 46, when the suture retriever 12 is removed from the bone tunnel. The suture buttress 14 is thus left in position within the bone tunnel as the suture retriever 12 is used to draw a suture through the suture buttress 14 and through the bone tunnel.

The slits 40 should be deep enough to cause the desired raised edges 46 when the resilient tube 26 is flexed, but not so deep as to compromise the structural integrity of the resilient tube 26. Otherwise, the depth of the slits 40 is not particularly limited and the slits 40 may have a depth that is less than the wall thickness 38 of the resilient tube 26, or the slits 40 may be deeper than the wall thickness 38 so that the slits 40 extend into the interior of the tube 26.

One of ordinary skill in the art will appreciate that a variety of other external fastening elements may be utilized to secure the suture buttress within a bone tunnel. Examples of suture buttresses having other external fastening elements are illustrated in FIGS. 4 and 5. Suture buttress 50 of FIG. 4 has a resilient hollow tube 51 with two resilient circumferential flanges 52, 54 formed on the outer surface 56 of resilient tube 51. One flange is formed adjacent to each of the opposed ends 58, 60 of the resilient tube 51. A person of ordinary skill in the art will appreciate that more or fewer flanges may be used and that the location of the flanges may be varied as necessary to achieve the purpose of the invention. The suture buttress 62, illustrated in FIG. 5, includes portions of the resilient hollow tube 63 adjacent to each of the opposed ends 64, 66 that are folded over onto outer surface 68 of the tube 63. The suture buttresses 50, 62 of FIGS. 4 and 5 may be applied using the suture retriever 12 illustrated in FIG. 1.

An additional suture buttress 200 of the invention is illustrated in FIG. 13. The suture buttress 200 includes a hollow tube 220, a circumferential flange 230, and an external securing element 240. The tube 220 has an outer surface 222 and opposed proximal and distal ends 224, 226.

The tube 220 further includes an inner lumen or passageway 232. In the embodiment of FIGS. 13–16, the inner lumen 232 may be tapered from the distal end 226 to the proximal end 224. The inner lumen 232 has a first diameter 236 at the distal end 226 and a second diameter 238 at the proximal end 224. The inner lumen 232 at its smallest diameter should be large enough to allow the tube 220 to be removably and replaceably disposed on a suture retriever 260 as shown in FIG. 20, and large enough to allow a suture to be drawn through the tube 220. In addition, the diameters must be selected so that, with an appropriate wall thickness 239, the tube 220 will fit within a suitably sized bone tunnel.

Generally, for use in rotator cuff repair surgery, the first diameter 236 at the distal end is between 0.070 and 0.100 inch and the second diameter 238 of the tube 220 at the proximal end is between about 0.060 and 0.085 inch. The wall thickness 239 is between about 0.010 and 0.040 inch. The tube 220 also has a constant outer diameter 237 in the range of about 0.1 to 0.2 inch.

Referring to FIGS. 13–20, the suture buttress 200 may be provided with an external securing element or tab 240 that is effective to secure it within a bone tunnel. The exemplary suture buttress 200 is provided with at least one tab 240 disposed in proximity to the proximal end 224, along the outer surface 222 of the tube 220 for this purpose. Although the exemplary embodiment is shown with three tabs, less than three or more than three tabs my be used to secure the buttress within the bone tunnel. The at least one tab 240 projects outward from the outer surface 222 of the tube 220, at an angle generally transverse to a longitudinal axis 244 of the tube 220. While the at least one tab 240 may project outward from the outer surface at any angle that is suitable to allow the tabs 240 to fold down upon insertion of the suture buttress within a bone tunnel, the tabs 240 will generally extend outward at an angle of about 90°. In this position, tabs 240 can penetrate or extend into the surface of the bone tunnel when deployed to securely fasten the suture buttress 200 therein.

As shown in FIG. 17, the tube 220 may include thin slits 252 formed in the outer surface 222 of the tube 220 adjacent to both sides (one shown) of the base of each tab 240 so that the tabs are easily deformed and flexed. Typically, the tabs 240 will be pressed back and recessed into cut-outs 228, positioned to provide clearance for the tabs 240 to deform, to allow the tube 220 to slide into a bone tunnel when urged in a first direction 301 into a bone tunnel by a surgeon, as discussed in more detail later herein. The slits 252 should be deep enough to allow the tab to bend and deform without detaching from the tube 220, but not so deep as to compromise the structural integrity of the tube 220. Otherwise, the depth of the slits 252 is not particularly limited and the slits 252 may have a depth that is less than the wall thickness 239 of the tube 220, or the slits 252 may be deeper than the wall thickness 239 so that the slits 252 extend into the interior of the tube 220. Generally, the slits 252 may be thin, having a thickness of about 0.005 to 0.010 inch.

Tab 240 may be formed by cutting out or otherwise deforming a portion of the outer surface 222 of the tube 220, by attachment of a separate tab piece to the outer surface 222, injection molded in place, or in some other manner that may be selected by a person of ordinary skill in the art. In an exemplary embodiment, each tab has a width 246 of about 0.02 to 0.04 inch, a thickness 248 of 0.02 inch to 0.03 inch and a height 250 of about 0.03 to 0.05 inch. The tabs may be constructed of the same materials as recited above for construction of the tube 220, such as PDS.

The suture buttress 200 of the present invention may also have a resilient circumferential flange 230 formed on the outer surface 222 of tube 220 to further secure the suture buttress 200 within the bone tunnel, i.e. to prevent the suture buttress 200 from sliding further in a first direction 301 into the bone tunnel, and to provide extra strength at the lateral edge of the buttress 200. In the illustrated embodiment, the flange 230 is formed adjacent to the proximal end 224 of the tube 220, proximate to the at least one tab 240. A person of ordinary skill in the art will appreciate that more than one or even no flanges may be used and that the location of the flange(s) may be varied as necessary to achieve the purpose of the invention.

The flange 230 may be constructed of the same materials as recited above for construction of the tube 220, such as PDS. The flange 230 is angled by an amount $\delta$ with respect to a plane 232 that is transverse to a longitudinal axis 244 of the tube 220. While the angle $\delta$ may take on any value suitable to retain the suture buttress 10 within the bone tunnel, $\delta$ is preferably between about 0° and 45° and more preferably about 15°. In an exemplary embodiment, the angle displacement $\delta$ of the flange 230 is equal to the angular displacement $\theta$ of the tabs 240 with respect to a plane 242 that is transverse to a longitudinal axis of tube 220. While the angle $\theta$ may take on any value suitable to retain the suture buttress 10 within the bone tunnel, $\theta$ is preferably also between about 0° and 45°.

Generally, the suture buttress 200 as described herein is designed for use with a suture retriever 260, as shown in FIG. 20. The suture retriever 260 has an elongate member 262 having an outer surface 264 and a suture retrieving element 266 disposed at its distal end 268. The suture buttress 200 is removable and replaceably disposed on the outer surface 264 of the elongate member 262. As shown in FIG. 19 and 20, the suture buttress 200 may be preformed in a curved shape to conform to the shape of the elongate member 262 of the suture retriever 260. In an exemplary embodiment, the suture buttress has a radius of curvature in the range of about 0.300 to 0.600 inch and preferably, 0.434 inch.

In a further embodiment of the present invention, the suture buttress has pores formed on the outer surface thereof which may extend through the walls of the buttress. Alternatively, the suture buttress of the invention may be constructed of a porous material to facilitate and promote bone ingrowth. The bone ingrowth further secures the suture buttress within the bone tunnel by bonding with the pores on the outer surface. In an exemplary embodiment, the pores have a diameter of about 100 to 500 microns. The pores would cover at least a portion of the suture buttress, preferably up to about 50% of the total surface area of the tube. Such pores can be formed integrally during the injection molding process or using a secondary process, such as laser or mechanical drilling, after the buttress has been formed.

An additional suture buttress 400 of the invention is illustrated in FIGS. 23 to 25. Suture buttress 400 includes a hollow tube 402 having an outer wall 404, a central channel 406, a center line 408 extending through the channel 406, a distal or leading end 410 for insertion into a bone tunnel and a proximal or trailing end 412. The hollow tube 402 is bendable from an unbent position (shown in FIGS. 23 and 24) to a bent or curved position (shown in FIG. 25) having an outer radius 414 and an outer radial surface 416. The outer radial surface 416 defines a plurality of outer radial cut outs or slits 418 formed in the outer wall 404. The slits 418 each have a leading edge 420 and a trailing edge 422 corresponding to the leading end 410 and trailing end 412 of the tube 402. The outer radial slits 418 may extend past the centerline 408 of tube 402 and may be substantially perpendicular to centerline 408.

The outer radial surface 416 includes at least one projecting member 424 extending outward from the outer wall 404 and having sufficient strength to form a friction fit within a bone tunnel. Suture buttress 400 has a series of pyramidal projecting members 424 arranged so that the highest point 426 of all but one of the projections is adjacent the leading edge 420 of an outer radial slit 418. When buttress 400 is placed in a curved position, the leading edges 420 of slits 418 engage the inner walls of the bone tunnel to secure the buttress 400 against removal in a direction opposite to the direction of its insertion. In addition, each projecting member 424, moving from the leading end 410 of the hollow tube 402 to the trailing end 412, increases in size. Accordingly, the projecting members 424 that give rise to the greatest amount of friction within a bone tunnel are the last projecting members 424 to enter the tunnel, easing insertion of the suture buttress 400. While projecting members 424 are arranged as pyramidal projections that increase in height in the direction from leading 410 to trailing 412 end, the projecting members 424 may take on any shape that results in a secure fit of suture buttress 400 within a bone tunnel.

Suture buttress 400 may also include secondary slits 428 formed on a surface 430 of hollow tube 402 opposite to the outer radial surface 416. Secondary slits 428 may also extend past center line 408 and be perpendicular to center line 408. In addition, secondary slits 428 may be formed so that bounding walls of the slits angle away from each other when suture buttress 400 is in an unbent position (FIG. 24). The clearance provided by the secondary slits 428 allows easy placement of suture buttress 400 into a bent or curved position (FIG. 25). Suture buttress 400 may then be manufactured in an unbent position, taking advantage of manufacturing economies, but readily conform to curved bone tunnels. In one embodiment, at least one secondary slit 428 is provided between each two adjacent outer radial slits 418.

Suture buttress 400 may also include any of the features provided for other suture buttress embodiments described herein, including an angled circumferential flange 432 provided on the trailing end 412 of hollow tube 402, one or more resilient tabs 434, bone ingrowth pores or a tapered inner lumen. In addition, suture buttress 400 may be dimensioned similarly to other suture buttress embodiments described herein and may be adapted to be removably and replaceably disposed on a suture retriever such as suture retriever 12 for application in a bone tunnel.

A suture buttress system 70 may also include a suture buttress deployment tool 72 as illustrated in FIG. 6. The suture buttress deployment tool 72 has a handle 74 and a deployment element 76. The deployment element 76 may be removably and replaceably disposed on an outer surface 78 of the suture retriever 79 adjacent and proximal to a suture buttress 80. Because the suture buttress 80 can be deployed from the suture retriever using the deployment tool 72, the suture buttress 80 need not have an external fastening element. Also, because the deployment tool 72 may be used to urge the suture buttress 80 into a bone tunnel, it is not necessary to provide a suture buttress stop, such as the suture buttress stop 24 shown in FIG. 1, on the suture retriever 79.

The deployment element 76 of the suture buttress deployment tool 72 may be in the form of a partial or complete loop. In an embodiment in which the deployment element 76 is in the form of complete loop, the loop may be circular. Such a circular loop has an inner diameter large enough to slide over the outer surface 78 of the suture retriever 79. However, the inner diameter of the circular loop should be less than the outer diameter of the suture buttress 80 so that the circular loop can be used to push the suture buttress 80 off of the outer surface 78 of suture retriever 79.

The suture retrieving device 12 useful with the invention for retrieving or retrograding a suture or other ligature, is illustrated in FIGS. 7–11. This exemplary instrument includes a handle 82, an elongate member 16, a suture retaining element 20, an actuator 84 and a linking member 86 which connects the actuator 84 to the suture retaining element 20.

The exemplary handle 82 is elongate, generally cylindrical and has opposed proximal 88 and distal 90 ends. The shape and dimensions of the handle 82 may be selected by a person of ordinary skill in the art to allow the handle 82 to be suitably grasped by a surgeon in an operating environment.

The actuator 84 is slidably mounted on a side wall 92 of the handle 82. In the embodiment shown, the actuator 84 is rectangularly-shaped and includes a series of flanges 94 having varying heights and angled surfaces so as to be easily manipulated in either of two directions by a surgeon's thumb. The actuator 84 is mounted so as to slide in a direction substantially parallel to a longitudinal axis 96 of the suture retriever 12 and is movable between a first position (shown in FIG. 7), wherein the actuator 84 is closest to the proximal end 88 of the handle 82, and a second position (shown in FIG. 8), wherein the actuator 84 is closest to the distal end 90 of the handle 82. The actuator 84 may also be selectively positionable at an intermediate location between the first and second positions as illustrated in FIG. 9.

The actuator 84 communicates with the interior of the handle 82 through a transverse member 98. The transverse member 98 may extend through a rectangular slot (not shown) in the side wall 92 of the handle 82 along which the actuator 84 slides.

The transverse member 98 of the actuator 84 is connected to the linking member 86, which may be a rigid or semi-rigid rod. Preferably, the linking member 86 extends from the transverse member 98 in the interior of the handle 82 through the interior of the elongate member 16 to communicate with the suture retaining element 20.

Detents may be provided to lock the suture retriever 12 in the fully retracted and intermediate positions. These detents may suitably be provided by forming protuberances 100, 102 on the interior of the handle 82 corresponding to the fully retracted and intermediate positions respectively. A biased member 104 attached to the transverse member 98 of the actuator 84 has a recess 106 which corresponds to the shape of the protuberances 100, 102. Accordingly, when the actuator 84 passes into the first or intermediate position, a detent is achieved.

The distal end 22 of the elongate member 16 may extend at various angles and with various curvatures. For example, the distal end 22 of the elongate member 16 is curved and sweeps though an arc of approximately 180°. The suture retaining element 20 extends at an angle β that is approximately 135° with respect to the longitudinal axis 96 of the suture retriever 12. The distal end 22 of the elongate member 16 may also take on other configurations which may be selected by a person of ordinary skill in the art for the intended use of the suture retriever 12.

The suture retaining element 20 may be made from any flexible material suitable for surgical use including metals such as stainless steel or super elastic nickel-titanium (NITINOL), or plastic materials having elastic properties such as polyester, polypropylene or nylon. The suture retaining element 20 may be formed into a wire loop from a single, continuous wire element, or it may be formed using two wire elements joined at a distal portion of each.

The suture retaining element 20, illustrated in its extended position in FIG. 8, has two leg segments 108, 110. Beginning at a proximal end 112 of the suture retaining element 20 and moving distally, the leg segments 108, 110 diverge from one another, reach a point of maximum width therebetween, then converge to meet at a distal end 114 of the suture retaining element 20. The suture retaining element 20 thereby takes on a quadrangular or diamond shape when extended. In its extended position, the suture retaining element 20 has a maximum width between the leg segments 108, 110 in the range of approximately 0.100 to 0.800 inch, and more preferably about 0.400 inch.

The suture retaining element 20 may also be retracted to an intermediate position as shown in FIG. 11. As the actuator 84 is moved from its second or distal-most position to the intermediate position, the diverging portions of the two leg segments 108, 110 contact the inner wall 116 of the distal end 22 of the elongate member 16. This causes the quadrangular shaped wire loop suture retaining member 20 to compress, or fold up, as it is retracted into the elongate member 16. When the actuator 84 reaches the intermediate position, a small portion of the suture retaining element 20 remains extended beyond the distal end 11 of the elongate member 16 and thereby defines a region 118 within the suture retaining member 20 where a suture may be retained. The retained suture may then be drawn through a suture buttress 14 by the suture retriever 12. In this partially retracted position, the width of the suture retaining element 20 should be sufficient to slidably retain a suture within the suture retaining element 20. This width is generally in the range of about 0.020 to 0.250 inch, and more preferably is approximately 0.0675 inch. In this position, the suture retaining element may generally extend approximately 0.0675 to 0.250 inch, and more preferably extends about 0.125 inch from the distal end 22 of the elongate member 16.

Moving the actuator 84 to its first, proximal-most position fully retracts the suture retaining element 20 within the distal end 22 of the elongate member 16 as shown in FIG. 7.

The suture retaining device of the invention may utilize other suture retaining element configurations, such as a two-jaw suture retaining element or a suture retaining element consisting of two wire-like members. Examples of suture retaining elements known in the art may be found, for example, in U.S. Pat. Nos. 4,779,616; 5,250,054; 5,364,410; 5,499,991; 5,501,692; 5,562,685; 5,569,269 and 5,573,542.

An additional suture buttress system 120 having an internal tube delivery scheme is illustrated in FIG. 12. The suture buttress system 120 includes a suture buttress 122 that is at least partially disposed inside the distal end 123 of the elongate member of a suture retriever. In this embodiment, the leg portions 108, 110 extend proximally through the suture buttress 122 and form buttress deployment elements 124, 126 which push the suture buttress 122 out from its position inside the distal portion 123 and into a bone tunnel. External fastening elements, as described above, may be provided on the suture buttress 122 to retain it within the bone tunnel.

The suture buttress system may be employed in a variety of surgical applications, particularly those using a bone tunnel to attach soft tissue to a bone using one or more sutures. An exemplary procedure for using the suture buttress system with a bone tunnel begins with the step of preparing the soft tissue to be attached to the bone by resecting damaged portions and attaching at least one suture thread to the tissue.

A bone tunnel is then formed in proximity to the anatomic attachment point of the soft tissue to the bone. The tunnel is formed by piercing the cortical bone tissue at each end of the tunnel using a device such as a cortical bone punch or a drill.

Referring to FIGS. 21 and 22, a circular bone rasp 290 may be used to complete the tunnel through subcortical bone. The rasp 290 is elongate and has opposed proximal ends 298 and distal ends 300. The rasp 290 may have a handle portion proximate the proximal end 298 and a cutting portion 310 proximate the distal end 300. The cutting portion 310 may have teeth on its inner surface and/or outer surfaces which can be used to smooth the subcortical bone and sharp cortical bone edges. Preferably, the cutting portion 310 has a radius of curvature to match the radius of curvature of the suture buttress, as described earlier herein. In addition, the cutting portion 310 may have a circular cross section having same diameter as the suture buttress, ensuring a close fit of the buttress in the bone tunnel formed with bone rasp 290. The shape and dimensions of the handle portion 294 may be selected by a person of ordinary skill in the art to allow the handle 294 to be suitably grasped by a surgeon in an operating environment.

A suture buttress system, such as suture buttress system 10 illustrated in FIG. 1, is inserted, distal end 22 first and with the suture retaining element 20 retracted, into the end of the bone tunnel opposite the soft tissue. The suture buttress system 10 is inserted until the suture buttress 14 is fully disposed within the bone tunnel and the distal end 22 of the suture retriever 16 reaches the opposite end of the tunnel. The suture retaining element 20 is used to grasp a suture by extending the suture retaining element 20 and directing the suture therethrough. The suture retaining element 20 is then retracted to its intermediate or retracted position as appropriate to slidingly engage or snugly engage the suture. The suture retriever 16 is then removed from the bone tunnel so as to draw the suture through the tunnel and the suture buttress 14 while leaving the suture buttress 14 in place within the tunnel. The suture is then secured in any manner known to one of ordinary skill in the art in order to secure the soft tissue to the bone.

Where the suture buttress 200 (shown in FIGS. 13–20) is employed, the suture buttress 200 is inserted until the suture buttress 200 is fully disposed within the bone tunnel and the distal end 226 of the suture retriever 260 reaches the opposite end of the tunnel. During insertion of the suture buttress 200, the tabs 240 recess into cut-outs 228 on the outer surface 222 of the tube 220. The suture retrieving element 266 is then used to grasp a suture by extending the suture retrieving element 266 and directing the suture, not shown, therethrough. The suture retrieving element 266 is then retracted as appropriate to slidingly engage or snugly engage the suture. The suture retriever 260 is then removed from the bone tunnel so as to draw the suture through the tunnel and the suture buttress 200 while leaving the suture buttress 200 in place within the tunnel. The suture is then secured in any manner known to one of ordinary skill in the art in order to secure the soft tissue to the bone.

Once the suture buttress 200 has been inserted into a bone tunnel, the tabs 240, previously recessed in cut-out 228, spring outward to engage or penetrate into the inner surface of the bone tunnel, which typically includes low density trabecular bone and soft marrow. The raised tabs 240 thereby prevent the suture buttress 200 from sliding out of the bone tunnel in a second direction 302, substantially opposed to the first direction 301, when the suture retriever 260 is removed from the bone tunnel. The suture buttress 200 is thus left in position within the bone tunnel as the suture retriever 260 is used to draw a suture through the suture buttress 200 and through the bone tunnel.

When a suture buttress of the invention is inserted into a curved bone tunnel, such as a bone tunnel produced by rasp 290, the buttress preferably extends substantially through the tunnel to prevent a suture from damaging the inner walls of the curved portion of the tunnel.

The procedure as described above is particularly useful reattaching an injured rotator cuff tendon to the proximal humerus, however, a person of ordinary skill in the art will be able to apply the system, buttress and procedure of the invention in a variety of surgical situations.

It will be understood that the foregoing is only illustrative of the principles of the invention, and that various modifications can be made by those skilled in the art without departing form the scope and spirit of the invention. All references cited herein are expressly incorporated by reference in their entirety.

What is claimed is:

1. A suture buttress, comprising:
   a hollow tube having an outer wall, a central channel, a center line extending through the channel, a leading end for insertion into a bone tunnel and a trailing end;
   the hollow tube being bendable into a curved tube having an outer radius and an outer radial surface, the outer radial surface defining a plurality of slits formed in the outer wall, the slits having a leading edge and a trailing edge corresponding to the leading end and trailing end of the tube;
   at least one projecting member integral with and extending outward from the outer wall, the at least one projecting member being sufficiently strong to form a friction fit within a bone tunnel.

2. The suture buttress of claim 1, wherein the projecting member is a pyramidal projection having a highest point adjacent to a leading edge of a slit formed in the outer radial surface.

3. The suture buttress of claim 1, wherein a plurality of projecting members are provided, each projecting member being larger than the adjacent projecting member in the trailing direction.

4. The suture buttress of claim 1, wherein the at least one slit is substantially perpendicular to the center line and extends past the center line.

5. The suture buttress of claim 1, wherein at least one secondary slit is defined on a surface of the hollow tube opposite the outer radial surface.

6. The suture buttress of claim 5, wherein the at least one secondary slit extends beyond the center line.

7. The suture buttress of claim 5, wherein the at least one secondary slit is substantially perpendicular to the center line.

8. The suture buttress of claim 5, wherein at least one secondary slit is provided between each adjacent slit in the outer radial surface.

9. The suture buttress of claim 1, wherein a circumferential flange is provided on the trailing end of the hollow tube.

10. The suture buttress of claim 1, wherein the suture buttress further comprises at least one resiliently deformable tab disposed on the outer surface of the tube, the at least one tab being formed at an angle to a longitudinal axis of the tube and extending outward from the outer surface of the bone tunnel buttress.

11. The suture buttress of claim 10, wherein the at least one tab is disposed on the tube in proximity to the trailing end.

12. The suture buttress of claim 1, wherein the suture buttress is adapted to be removably and replaceably disposed on a suture retriever.

13. The suture buttress of claim 1, wherein the tube is dimensioned to extend substantially through the bone tunnel.

14. The suture buttress of claim 13, wherein the tube has a length of about 0.75 to 1.50 inches.

15. The suture buttress of claim 1, wherein the hollow tube has bone ingrowth pores formed on the outer wall thereof.

16. The suture buttress of claim 1, further comprising a suture retriever, wherein the hollow tube is adapted to be removably and replaceably disposed on the suture retriever, the projecting member of the bone tunnel buttress being effective to allow the bone tunnel buttress to slide into a bone tunnel in a first direction when urged into the bone tunnel by the suture retriever while preventing the bone tunnel buttress from sliding out of the bone tunnel in a second direction that is substantially opposed to the first direction upon removal of the suture retriever from the bone tunnel.

17. A method for attaching soft tissue to a bone comprising the steps of:
   forming a first hole at least through cortical bone tissue of the bone proximate to the soft tissue attachment site;
   forming a second hole at least through cortical bone tissue of the bone spaced a predetermined distance apart from the first hole;
   connecting the first hole and the second hole though subcortical bone tissue to form a tunnel in the bone;
   providing a suture buttress system comprising:
      a hollow tube having an outer wall, a central channel, a center line extending through the channel, a leading end for insertion into a bone tunnel and a trailing end;
      the hollow tube being bendable into a curved tube having an outer radius and an outer radial surface, the outer radial surface defining a plurality of slits formed in the outer wall and extending past the center line, the slits having a leading edge and a trailing edge corresponding to the leading end and trailing end of the tube;
      at least one projecting member extending outward from the outer wall, the at least one projecting member being sufficiently strong to form a friction fit within a bone tunnel;
   inserting the leading end of the suture buttress system into the bone tunnel and securing the buttress within the tunnel;

attaching a suture to the soft tissue and passing the suture through the bone tunnel and through the channel in the buttress; and securing the suture to secure the soft tissue to the bone.

18. The method of claim 17, wherein the projecting member is a pyramidal projection having a highest point adjacent to a leading edge of a slit formed in the outer radial surface.

19. The method of claim 17, wherein a plurality of projecting members are provided, each projecting member being larger than the adjacent projecting member in the trailing direction.

20. The method of claim 17, wherein the at least one slit is substantially perpendicular to the center line.

21. The method of claim 17, wherein at least one secondary slit is defined on a surface of the bendable tube opposite the outer radial surface.

22. The method of claim 21, wherein the at least one secondary slit extends beyond the center line.

23. The method of claim 21, wherein the at least one secondary slit is substantially perpendicular to the center line.

24. The method of claim 21, wherein at least one secondary slit is provided between each adjacent slit in the outer radial surface.

25. The method of claim 17, wherein a circumferential flange is provided on the trailing end of the hollow tube.

26. The method of claim 17, wherein the suture buttress system further comprises at least one resiliently deformable tab disposed on the outer surface of the tube, the at least one tab being formed at an angle to a longitudinal axis of the tube and extending outward from the outer surface of the bone tunnel buttress.

27. The method of claim 26, wherein the at least one tab is disposed on the tube in proximity to the trailing end.

28. The method of claim 17, wherein the tube is dimensioned to extend substantially through the bone tunnel.

29. The method of claim 28, wherein the tube has a length of about 0.75 to 1.50 inches.

30. The method of claim 17, wherein the hollow tube has bone ingrowth pores formed on the outer wall thereof.

31. The method of claim 17, wherein the suture buttress system further comprises a suture retriever, wherein the hollow tube is adapted to be removably and replaceably disposed on the suture retriever, the projecting member of the bone tunnel buttress being effective to allow the bone tunnel buttress to slide into a bone tunnel in a first direction when urged into the bone tunnel by the suture retriever while preventing the bone tunnel buttress from sliding out of the bone tunnel in a second direction that is substantially opposed to the first direction upon removal of the suture retriever from the bone tunnel.

32. The method of claim 17 for repairing a rotator cuff injury wherein the soft tissue is a rotator cuff tendon and the bone is a humerus.

* * * * *